(12) United States Patent
Astegher et al.

(10) Patent No.: US 9,151,809 B2
(45) Date of Patent: Oct. 6, 2015

(54) HALL SENSOR ARRANGEMENT FOR THE REDUNDANT MEASUREMENT OF A MAGNETIC FIELD

(75) Inventors: Berthold Astegher, Villach (AT); Helmut Wietschorke, Laberweinting (DE)

(73) Assignee: INFINEON TECHNOLOGIES AG, Neubiberg (DE)

( * ) Notice: Subject to any disclaimer, the term of this patent is extended or adjusted under 35 U.S.C. 154(b) by 260 days.

(21) Appl. No.: 13/249,301

(22) Filed: Sep. 30, 2011

(65) Prior Publication Data

US 2012/0081109 A1    Apr. 5, 2012

(30) Foreign Application Priority Data

Sep. 30, 2010    (DE) .......................... 10 2010 047 128

(51) Int. Cl.
    *G01R 33/06*    (2006.01)
    *G01R 33/07*    (2006.01)
(52) U.S. Cl.
    CPC ...................................... *G01R 33/07* (2013.01)
(58) Field of Classification Search
    CPC ... G01R 15/202; G01D 11/245; G01D 5/142; H01L 23/3121
    USPC ...................................... 324/251, 207.2, 249
    See application file for complete search history.

(56) References Cited

U.S. PATENT DOCUMENTS

| | | | |
|---|---|---|---|
| 5,146,201 A * | 9/1992 | Kimura et al. .............. | 338/32 H |
| 5,321,204 A * | 6/1994 | Ko ................................ | 257/686 |
| 5,783,463 A | 7/1998 | Takehashi et al. | |
| 6,479,987 B1 * | 11/2002 | Marx et al. .................. | 324/207.2 |
| 6,607,940 B2 * | 8/2003 | Yasunaga ...................... | 438/112 |
| 6,965,154 B2 * | 11/2005 | Abe et al. ...................... | 257/506 |
| 7,768,083 B2 * | 8/2010 | Doogue et al. ................ | 257/422 |
| 7,906,961 B2 | 3/2011 | Abwa et al. | |
| 8,093,670 B2 * | 1/2012 | Taylor ........................... | 257/427 |
| 2002/0067162 A1 * | 6/2002 | Dammkohler et al. .. | 324/207.21 |
| 2003/0116848 A1 * | 6/2003 | Cunningham et al. ........ | 257/747 |
| 2007/0040803 A1 * | 2/2007 | Dider et al. ................... | 345/161 |
| 2008/0012558 A1 | 1/2008 | Rossler et al. | |
| 2008/0150120 A1 * | 6/2008 | Nishimura et al. ........... | 257/690 |

(Continued)

FOREIGN PATENT DOCUMENTS

| | | | |
|---|---|---|---|
| DE | 19815906 A1 | | 10/1999 |
| DE | 19815906 A1 | * | 10/1999 |

(Continued)

OTHER PUBLICATIONS

English language abstract of EP 1382935 A1.

(Continued)

*Primary Examiner* — Tung X Nguyen
*Assistant Examiner* — Giovanni Astacio-Oquendo

(57) ABSTRACT

In various embodiments, a Hall sensor arrangement for the redundant measurement of a magnetic field may include a first Hall sensor on a top side of a first semiconductor substrate; a second Hall sensor on a top side of a second semiconductor substrate; a carrier having a top side and an underside; wherein the first Hall sensor is arranged on the top side of the carrier and the second Hall sensor is arranged on the underside of the carrier; and wherein the measuring area of the first Hall sensor projected perpendicularly onto the carrier at least partly overlaps the measuring area of the second Hall sensor projected perpendicularly onto the carrier.

18 Claims, 3 Drawing Sheets

(56) References Cited

U.S. PATENT DOCUMENTS

2009/0315547 A1* 12/2009 Abwa et al. .................. 324/244
2010/0109654 A1* 5/2010 Schneider et al. ......... 324/207.2
2014/0210479 A1* 7/2014 Rink et al. ................... 324/426

FOREIGN PATENT DOCUMENTS

| DE | 10315532 A1 | 11/2004 |
| DE | 102005060713 A1 | 6/2007 |
| DE | 102006032277 A1 | 1/2008 |
| EP | 1382935 A1 | 1/2004 |

OTHER PUBLICATIONS

English language abstract of DE 10315532 A1.
English language abstract of DE 19815906 A1.
IEC 61508-2/CDV, Annex E, Special architecture requirements for integrated circuits (ICs) with on-chip redundancy, pp. 76-81.
Melexis, Dual Programmable Linear Hall Effect Sensor MLX90277, Nov. 2006, 21 pages.

* cited by examiner

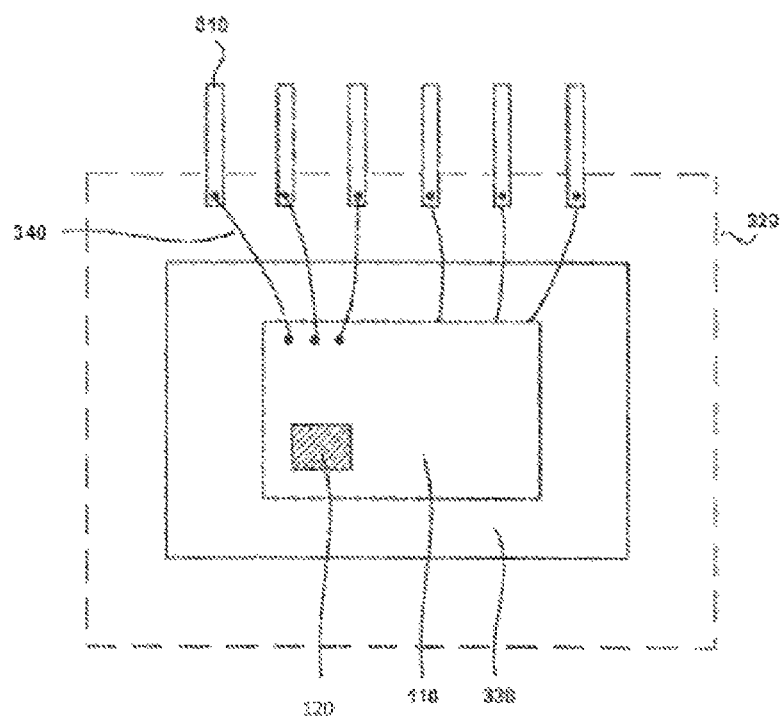

HALL SENSOR ARRANGEMENT FOR THE REDUNDANT MEASUREMENT OF A MAGNETIC FIELD

CROSS-REFERENCE TO RELATED APPLICATION

This application claims priority to German Patent Application Serial No. 10 2010 047 128.3, which was filed Sep. 30, 2010, and is incorporated herein by reference in its entirety.

TECHNICAL FIELD

Various embodiments relate to a Hall sensor arrangement for the redundant measurement of a magnetic field.

BACKGROUND

Magnetic field sensors have a broad field of use. Magnetic field sensors are often used in combination with magnetic field generators, such as simple magnets, to determine positions of mechanical components. In an automobile, magnetic field sensors are often used to determine positions of rotational components, such as shafts, or translational components, such as valves. Hall sensors are distinguished, in comparison with giant magnetoresistance (GMR) sensors, by the fact that Hall sensors measure the magnetic field component that is perpendicular to the Hall sensor.

A use in safety-relevant applications requires a very high operating safety of the components used, that is to say also a very high operating safety in the case of magnetic field sensors. As an example of the requirements made of safety-relevant systems, or components, IEC 61508 shall be cited, which finds application in the automotive industry.

Takehashi et al. disclose in U.S. Pat. No. 5,783,463 an arrangement and a method for realizing a multi-chip housing in order to obtain a lighter and smaller housing. This housing enables smaller and lighter electronic machines.

Strack et al. disclose in DE 198 15 906 a housing for a power semiconductor, and a larger surface for semiconductor chips is available in the component.

Außerlechner discloses in DE 103 15 532 a current sensor device of integrated embodiment. In this case, a structure through which current flows generates a magnetic field, such that a current is measured indirectly by way of the magnetic field generated by the current. The GMR sensors are connected to one another via an electrical connection. Since the magnetic field lines generated by the current enclose the current conductor, a magnetic field sensor is required which reacts to horizontal magnetic field lines with respect to the magnetic field sensor, such that the use of GMR sensors is required here.

The data sheet of the MLX90277 from Melexis describes a "Dual Programmable Linear Hall Effect Sensor" in which two discrete CMOS ICs are arranged in a single housing such that they are electrically insulated and independently programmable.

The use of magnetic field sensors in a safety-relevant area, such as an automobile, for example, necessitates dispensing with components which can adversely influence the lifetime of a magnetic field sensor, such as, for example, moisture-sensitive substances in a semiconductor housing.

The use of magnetic field sensors in a safety-relevant area, such as an automobile, for example, additionally requires redundant or partly redundant systems.

Despite the stringent requirements made of safety, reliability and redundancy, magnetic field sensors, particularly in an automobile, have to be inexpensive.

SUMMARY

In various embodiments, a Hall sensor arrangement for the redundant measurement of a magnetic field may include a first Hall sensor on a top side of a first semiconductor substrate; a second Hall sensor on a top side of a second semiconductor substrate; a carrier having a top side and an underside; wherein the first Hall sensor is arranged on the top side of the carrier and the second Hall sensor is arranged on the underside of the carrier; and wherein the measuring area of the first Hall sensor projected perpendicularly onto the carrier at least partly overlaps the measuring area of the second Hall sensor projected perpendicularly onto the carrier.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which:

FIG. 3 shows a plan view of a Hall sensor arrangement; and

DETAILED DESCRIPTION

Figure 1:
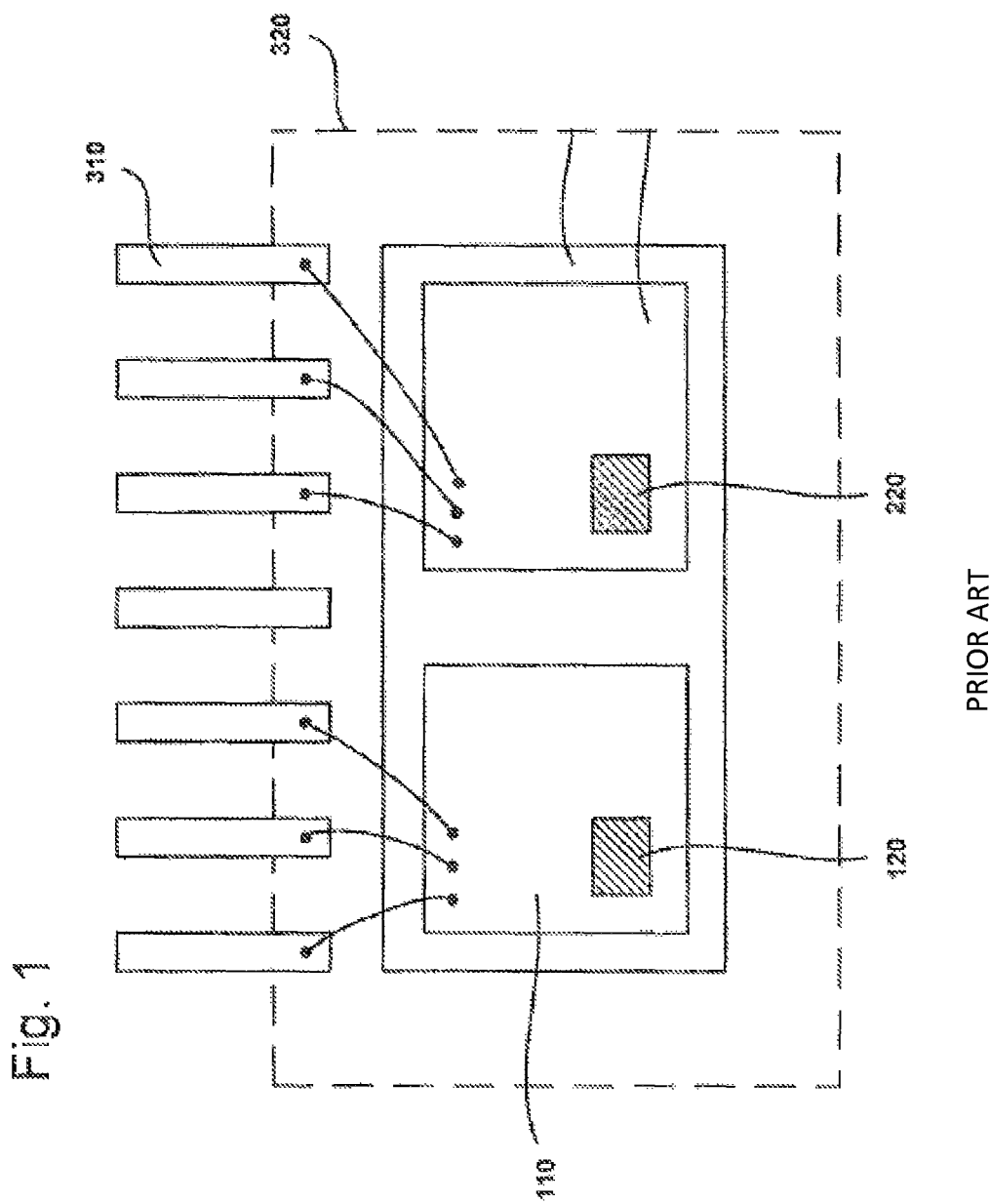
FIG. 1 shows a plan view of a known arrangement of Hall sensors.

The following detailed description refers to the accompanying drawings that show, by way of illustration, specific details and embodiments in which the invention may be practiced.

The word "exemplary" is used herein to mean "serving as an example, instance, or illustration". Any embodiment or design described herein as "exemplary" is not necessarily to be construed as preferred or advantageous over other embodiments or designs.

The word "over" used with regards to a deposited material formed "over" a side or surface, may be used herein to mean that the deposited material may be formed "directly on", e.g. in direct contact with, the implied side or surface. The word "over" used with regards to a deposited material formed "over" a side or surface, may be used herein to mean that the deposited material may be formed "indirectly on" the implied side or surface with one or more additional layers being arranged between the implied side or surface and the deposited material.

Various embodiments provide a magnetic field sensor which is redundant, reliable, safe and inexpensive.

A Hall sensor arrangement for the redundant measurement of a magnetic field may include a first Hall sensor on a top side of a first semiconductor substrate, a second Hall sensor on a top side of a second semiconductor substrate, and a carrier having a top side and an underside. The first Hall sensor is arranged on the top side of the carrier, and the second Hall sensor is arranged on the underside of the carrier. The Hall sensors are arranged in such a way that the measuring area of the first Hall sensor projected perpendicularly onto the carrier at least partly overlaps the measuring area of the second Hall sensor projected perpendicularly onto the carrier.

The Hall sensors are therefore arranged in such a way that the Hall sensors measure the same magnetic field lines of an externally applied magnetic field. Hall sensors measure the perpendicular component of the magnetic field lines that permeate the Hall sensors. The Hall sensor arrangement has the effect that the Hall sensors measure virtually the same magnetic field, such that the measurement results of the two Hall sensors are virtually redundant with respect to one another. Depending on the extent to which the measuring areas of the first Hall sensor and of the second Hall sensor projected perpendicularly onto the carrier overlap, partial or complete redundancy is present.

One effect of Hall sensors is that Hall sensors can be manufactured without a great outlay using an existing semiconductor technology, such that it is possible to integrate a Hall sensor with a complex integrated circuit in one semiconductor substrate. In contrast to this, a GMR sensor is applied on an integrated circuit after the latter has been passivated by suitable means. The GMR sensor per se has to be passivated by further suitable means. These passivation layers have the disadvantage that they react more sensitively to moisture than the final passivation of the semiconductor substrate.

The Hall sensor arrangement according to various embodiments may have the effect that the Hall sensors, with their at least partly overlapping Hall sensors, measure the same magnetic field components of an externally applied magnetic field since an externally applied magnetic field flows equally through both Hall sensors. The Hall sensor arrangement may therefore have the effect that complete redundancy of the Hall sensors can be achieved. The Hall sensor arrangement may have the effect that the housing for accommodating the Hall sensor arrangement is small and compact. A small housing greatly extends usability, with regard to the increasing miniaturization of electronic circuit boards and assemblies. A small housing, solely by virtue of its size, is exposed to small mechanical loads, such as shear and bending forces, which increases the reliability of such a Hall sensor arrangement.

A further effect of the Hall sensor arrangement may be that no film has to be applied between the two Hall sensors, since both Hall sensors can be fixedly applied on a substrate. Dispensing with mounting aids results in a flat housing that is balanced in its entirety.

Moisture-sensitive substances such as, for example, die attach films, polyimides as passivation layers can foster the destruction of a housing. Dispensing with such exemplary mounting aids affords the further advantage that the Hall sensor arrangement is insensitive to moisture since there are just no housing constituents which absorb moisture or are sensitive to moisture. By dispensing therewith, the housing of the Hall sensor arrangement remains small and compact. A further effect of the Hall sensor arrangement may result from the fact that only short bonding wires are necessary for electrically connecting the upper Hall sensor to the contacts of the housing. A further effect of a Hall sensor arrangement according to various embodiments may be that this Hall sensor arrangement is very well balanced and not out of balance, which has a positive effect on the thermomechanical behaviour and thus also has a positive effect on reliability.

In various embodiments of the Hall sensor arrangement for the redundant measurement of a magnetic field, the Hall sensors may be completely enclosed by a moulding compound. An effect afforded is that no further passivations have to be used alongside passivations used for the standard passivation of the Hall sensors, e.g. oxide, nitride, imide passivations on the semiconductor substrate. A further effect afforded is that, alongside a standard moulding compound, neither a special moulding compound nor a special method has to be used for enclosing the Hall sensor arrangement.

In accordance with various embodiments, the first and the second semiconductor substrate of the Hall sensor arrangement for the redundant measurement of a magnetic field can have an integrated circuit.

The first and the second semiconductor substrate of the Hall sensor arrangement for the redundant measurement of a magnetic field can be arranged in a manner rotated relative to one another.

The semiconductor substrates of the Hall sensor arrangement for the redundant measurement of a magnetic field have an underside lying opposite the top side, wherein semiconductor substrates may be arranged with their undersides on the carrier.

The undersides of the semiconductor substrates of the Hall sensor arrangement for the redundant measurement of a magnetic field may be fixed on the carrier by means of an insulating adhesive.

The Hall sensor arrangement may have contact strips, and the Hall sensors may have electrical contacts for providing a Hall signal. The electrical contacts of the first and of the second Hall sensor are connected to dedicated contact strips. By virtue of this arrangement, the Hall sensors may be connected independently of one another, such that the measured values of the Hall sensors may also be read out independently of one another. The Hall sensors may therefore be read in a redundant fashion. An integrated circuit may set the operating parameters of the Hall sensors. The first semiconductor substrate may have only one Hall sensor, while the second semiconductor substrate has an integrated circuit for driving the first and the second Hall sensor.

The semiconductor substrates may have electrical contacts for providing electrical signals, wherein the electrical contacts of the first and of the second semiconductor substrates are connected to dedicated contact strips. By virtue of this arrangement, not only the Hall sensors but also the integrated circuits may be connected independently of one another, such that both the measured values of the Hall sensors and the settings of the Hall sensors may be read out and set independently of one another. The semiconductor substrates with the Hall sensors and the integrated circuits may be identical. Complete redundancy is achieved by virtue of this arrangement.

The contact strips for electrically connecting the first and the second semiconductor substrate may be arranged on opposite sides of the carrier. As a result, a symmetrical contact-making arrangement arises and the dimensions of the housing are somewhat smaller than in the case where the contact strips are led out on one side. Moreover, a genuine surface-mount device conforming (SMD-conforming) component arises in this way. The arrangement of all the contacts on one side may have the effect, when a component is soldered on, that the housing body rises up (tombstone effect), which, given the small installation height, may lead to problems for the customer.

Figure 2:
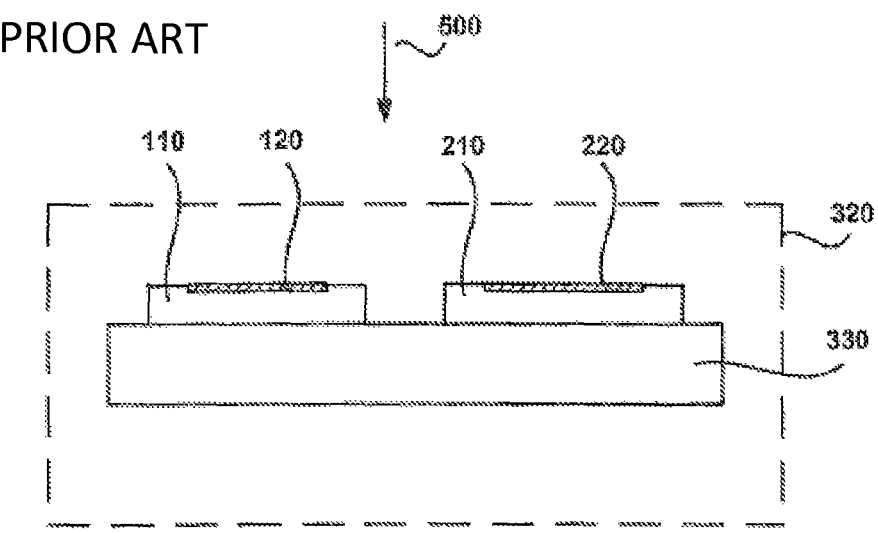
FIG. 2 shows a side view in section of a known arrangement of Hall sensors.

FIG. 1 and FIG. 2 show two Hall sensors 120, 220 on two semiconductor substrates 110, 210 arranged on one side of a carrier 330. The Hall sensors 120, 220 do not measure the same magnetic field 500, such that this arrangement is only virtually redundant. This arrangement has the disadvantage that the housing 320 for accommodating both Hall sensors 120, 220 has to be chosen to be correspondingly larger than in the case of an individual Hall sensor. A large housing 320 greatly restricts usability, also with regard to the increasing miniaturization of electronic circuit boards and assemblies. A larger housing 320, moreover, solely by virtue of its size, is exposed to larger mechanical loads, such as shear and bending forces, which reduces the reliability of such a Hall sensor arrangement.

Figure 4:
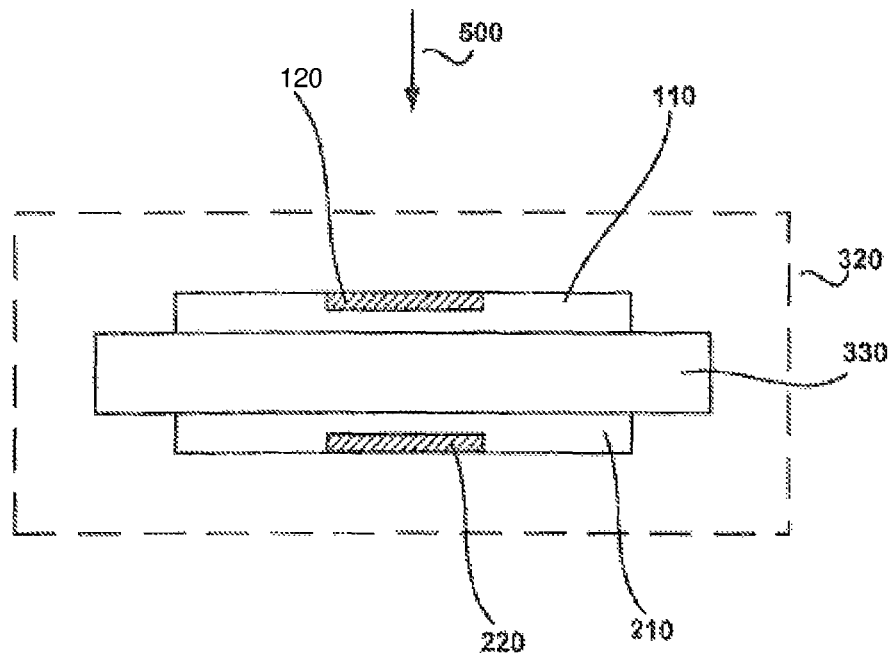
FIG. 4 shows a side view in section of a Hall sensor arrangement.

FIG. 3 and FIG. 4 show a plan view and a side view in section of an exemplary embodiment of a Hall sensor arrangement according to various embodiments. The various embodiments of a Hall sensor arrangement may have a carrier 330, on which the semiconductor substrates 110, 210 are arranged by their rear sides. Hall sensors 120, 220 are arranged on the top sides of the semiconductor substrates 110, 210. The side view in FIG. 4 shows that the Hall sensors 120, 220 for measuring a magnetic field 500 are arranged in an overlapping fashion. The semiconductor substrates 110, 210 are enclosed by a moulding compound that determines the external dimensions of the housing 320. Contact strips 310 are provided for the purpose of electrical connection, said contact strips being connected to the semiconductor substrates 110, 210 by means of bonding wires 340.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A Hall sensor arrangement for the redundant measurement of a magnetic field, the Hall sensor arrangement comprising:
    a first Hall sensor on a top side of a first semiconductor substrate;
    a second Hall sensor on a top side of a second semiconductor substrate;
    a carrier having a top side and an underside;
    wherein the first Hall sensor is arranged on the top side of the carrier and the second Hall sensor is arranged on the underside of the carrier; and
    wherein the measuring area of the first Hall sensor projected perpendicularly onto the carrier substantially completely overlaps the measuring area of the second Hall sensor projected perpendicularly onto the carrier providing redundant measurement of the magnetic field component perpendicular to the carrier.

2. The Hall sensor arrangement for the redundant measurement of a magnetic field according to claim 1, wherein a moulding compound completely encloses the first Hall sensor and the second Hall sensor.

3. The Hall sensor arrangement for the redundant measurement of a magnetic field according to claim 2, wherein the moulding compound completely enclosing the first Hall sensor and the second Hall sensor has a thickness that is substantially equal on the topside and the underside of the carrier, respectively, to provide a substantially thermomechanically balanced housing.

4. The Hall sensor arrangement for the redundant measurement of a magnetic field according to claim 1, wherein the first and the second semiconductor substrate have an integrated circuit.

5. The Hall sensor arrangement for the redundant measurement of a magnetic field according to claim 4, wherein the Hall sensor arrangement has contact strips; and wherein the integrated circuit of the first semiconductor substrate and the integrated circuit of the second semiconductor substrate are independently connected to dedicated contact strips.

6. The Hall sensor arrangement for the redundant measurement of a magnetic field according to claim 5, further comprising:
    a housing, wherein the contact strips of the first semiconductor substrate are arranged in a manner lying opposite the contact strips of the second semiconductor substrate on the housing.

7. The Hall sensor arrangement for the redundant measurement of a magnetic field according to claim 4, wherein the Hall sensor arrangement has contact strips; and wherein the first Hall sensor and the second Hall sensor are independently connected to dedicated contact strips.

8. The Hall sensor arrangement for the redundant measurement of a magnetic field according to claim 4, wherein the Hall sensor arrangement has contact strips; and wherein the first Hall sensor, the second Hall sensor, the integrated circuit of the first semiconductor substrate, and the integrated circuit of the second semiconductor substrate, are independently connected to dedicated contact strips.

9. The Hall sensor arrangement for the redundant measurement of a magnetic field according to claim 4, wherein a Hall signal from the first Hall sensor is measured by the integrated circuit of the first semiconductor substrate, which provides a measured value of the first Hall sensor by the integrated circuit of the first semiconductor substrate; and a Hall signal from the second Hall sensor is measured by the integrated circuit of the second semiconductor substrate, which provides a measured value of the second Hall sensor by the integrated circuit of the second semiconductor substrate.

10. The Hall sensor arrangement for the redundant measurement of a magnetic field according to claim 9, wherein the Hall signal from the first Hall sensor and the Hall signal from the second Hall sensor are read out independently of one another.

11. The Hall sensor arrangement for the redundant measurement of a magnetic field according to claim 9, wherein the measured value of the first Hall sensor by the integrated circuit of the first semiconductor substrate and the measured value of the second Hall sensor by the integrated circuit of the second semiconductor substrate are read out independently of one another.

12. The Hall sensor arrangement for the redundant measurement of a magnetic field according to claim 9, wherein the Hall signal from the first Hall sensor, the Hall signal from the second Hall sensor, the measured value of the first Hall sensor by the integrated circuit of the first semiconductor substrate, and the measured value of the second Hall sensor by the integrated circuit of the second semiconductor substrate, are read out independently of one another.

13. The Hall sensor arrangement for the redundant measurement of a magnetic field according to claim 1, wherein the first and the second semiconductor substrate are arranged in a manner rotated relative to one another.

14. The Hall sensor arrangement for the redundant measurement of a magnetic field according to claim 1, wherein the first and the second semiconductor substrate have an underside lying opposite the top side; wherein the first and the second semiconductor substrate are arranged with their undersides on the carrier.

15. The Hall sensor arrangement for the redundant measurement of a magnetic field according to claim 1, wherein the undersides of the first and of the second semiconductor substrate are fixed on the carrier by means of an insulating adhesive.

16. The Hall sensor arrangement for the redundant measurement of a magnetic field according to claim 1, wherein the Hall sensor arrangement has contact strips and the first and the second semiconductor substrates have electrical contacts for providing a Hall signal; wherein the electrical contacts of the first and of the second semiconductor substrates for providing electrical signals are connected to dedicated contact strips.

17. The Hall sensor arrangement for the redundant measurement of a magnetic field according to claim 16, wherein the contact strips of the first semiconductor substrate are arranged in a manner lying opposite the contact strips of the second semiconductor substrate on the housing.

18. The Hall sensor arrangement for the redundant measurement of a magnetic field according to claim 1, wherein the first and the second semiconductor substrates have electrical contacts for providing electrical signals; wherein the electrical contacts of the first and of the second semiconductor substrate for providing electrical signals are connected to dedicated contact strips.

* * * * *